United States Patent
Fraga et al.

(10) Patent No.: US 8,962,882 B2
(45) Date of Patent: Feb. 24, 2015

(54) LACTIC ACID DIRECT SYNTHESIS PROCESS

(71) Applicants: Petróleo Brasileiro S.A.—Petrobras, Rio de Janeiro (BR); Int—Instituto Nacional de Tecnologia, Rio de Janeiro (BR)

(72) Inventors: Marco André Fraga, Rio de Janeiro (BR); Tatiana Vieira Galvão, Rio de Janeiro (BR); Simone Maria De Rezende, Rio de Janeiro (BR); Andrea Maria Duarte De Farias, Rio de Janeiro (BR); Alexandre Barros Gaspar, Rio de Janeiro (BR); Marlito Gomes Junior, Petropolis (BR); Carlos René Klotz Rabello, Rio de Janeiro (BR); Bernardo Galvão Siqueira, Rio de Janeiro (BR); Raphael Bezerra De Menezes, Rio de Janeiro (BR)

(73) Assignees: Petroleo Brasileiro S.A.—Petrobras, Rio de Janeiro (BR); Int—Instituto Nacional de Tecnologia, Rio de Janeiro (BR)

( * ) Notice: Subject to any disclaimer, the term of this patent is extended or adjusted under 35 U.S.C. 154(b) by 0 days.

(21) Appl. No.: 14/087,203

(22) Filed: Nov. 22, 2013

(65) Prior Publication Data

US 2014/0155651 A1 Jun. 5, 2014

(51) Int. Cl.
*C07C 51/235* (2006.01)

(52) U.S. Cl.
CPC .................................. *C07C 51/235* (2013.01)
USPC ........................................................ 562/538

(58) Field of Classification Search
USPC ........................................................ 562/538
See application file for complete search history.

(56) References Cited

U.S. PATENT DOCUMENTS

2014/0148616 A1* 5/2014 Fraga et al. .................. 562/538

FOREIGN PATENT DOCUMENTS

| CN | 101225041 A | 7/2008 |
| EP | 2 184 270 A1 | 5/2010 |

\* cited by examiner

*Primary Examiner* — Yong Chu
*Assistant Examiner* — Sonya Wright
(74) *Attorney, Agent, or Firm* — Sughrue Mion, PLLC

(57) ABSTRACT

This invention concerns a process for obtaining lactic acid in a single stage by direct oxidation in an aqueous medium of 1,2-propanediol in the presence of a mixture of heterogeneous catalysts, in conditions of low temperature and low pressure. The reaction takes place in the presence of oxygen and a mixture of heterogeneous catalysts, consisting of a first catalyst of noble metal supported in metallic oxide, and a second basic solid catalyst. The mixture of catalysts is easily recovered by filtration at the end of the process, to be reused. The lactic acid is obtained directly, with selectivity between 50% and 97%.

17 Claims, No Drawings

LACTIC ACID DIRECT SYNTHESIS PROCESS

THE FIELD OF THE INVENTION

This invention concerns a process for obtaining lactic acid in a single stage by direct oxidation in an aqueous medium of 1,2-propanediol in the presence of a mixture of heterogeneous catalysts. More particularly, the process refers to the synthesis of lactic acid by direct oxidation in conditions of low temperature and low pressure, in the presence of a physical mixture of heterogeneous catalysts, with a first catalyst being based on a noble metal supported in metallic oxide with a second basic catalyst.

BACKGROUND OF THE INVENTION

With the increase of worldwide production of biodiesel, a large number of studies have been carried out with the objective of absorbing the excess glycerine available on the market, about 10% of the total production of biodiesel, which reduces its economic value, and at the same time generating new products with higher added value.

In a first phase, products such as 1,2-propanediol can be obtained from glycerine. This raw material, which is also available in abundance, has become important in obtaining chemical products which are of great interest currently.

Lactic acid is an important raw material for the chemical industry currently and is widely consumed in different industrial sectors. It has application in the foods industry in the fabrication of various products, for example, such as yoghurt and cheese. It is also used in the cosmetics industry as a wetting agent; in the textile industry as a mordant and for curing of leather.

The modern petrochemical industry, which is now facing the challenge of seeking sustainable means to provide green products of low environmental impact, is looking to lactic acid as one of the important raw materials for the production of biodegradable materials, particularly in the obtaining of poly(lactic acid)—PLA.

PLA is a biodegradable, compostable and biocompatible polymer with a vast range of applications. Besides its well established use in the medical area, its use in plastic packaging has received increasing attention, which in being considered a green polymer, minimises impacts on the environment.

Lactic acid can be produced by different means, and is an example of a classic process of production based on the reaction between acetaldehyde and cyanic acid followed by the stage of hydrolysis with sulphuric acid or by the reaction of carbon monoxide with formaldehyde in water at high pressures using hydrofluoric acid as a catalyst. These means of synthesis use highly hazardous and toxic products, take place in a homogeneous medium, generate polluting liquid waste with a high environmental impact and entail processes with a high cost. As a consequence, lactic acid is fabricated commercially these days by fermentation of sugars.

However, the fermentation or biochemical processes have disadvantages in taking a long time and being of quite high cost, as they make use of complex micro-organisms which require special care for their growth, development and maintenance, involving large volume equipment which significantly increases the cost of production.

Lactic acid can also be obtained by the chemical transformation of other sources. The academic technical literature for example shows a process where glycerine is used in a reaction which takes place in an alkaline medium in homogeneous phase and under hydrothermic conditions [H. Kishida, F. Jin, Z. Zhou, T. Moriya, H. Enomoto, Chem. Lett. 34 (2005) 1560-1561]. Although the yields of lactic acid reach about 90%, the reactions take place at very high temperatures, at around 300° C., and considerably high pressures. Furthermore, the final product obtained is the derived salt of lactic acid, lactate, as a function of the addition of alkaline solution to the reaction medium. Thus, the stage of hydrolysis with an inorganic acid at the end of the synthesis is required to obtain the free lactic acid. These conditions entail processes of high cost as well as high energy cost, also requiring equipment constructed with special materials in order to avoid corrosion of the reactors due to the high concentration of hydroxide.

Selective oxidation reactions of the primary hydroxyl of the 1,2-propanediol to lactic acid in an aqueous medium using a heterogeneous catalyst have also been reported in the literature [M. Hong, N. Xin, C. JiaYing, C. Chen, G. Jin, M. Hong, X. Jie, Sci. China Chem., 53 (2010) 1497-1501]. In these processes, the authors describe the use of gold catalysts supported in $Mg(OH)_2$, which lead to 94.4% conversion of 1,2-propanediol, 89.3% selectivity of lactic acid, resulting in 84.3% yield of acid after 6 hours of reaction. However, in this process there is also the need to add a solution of NaOH, thus leading to lactic acid salt as the final product. The authors describe the use of a molar ratio between NaOH and 1,2-propanediol equal to 2 and the process takes place at quite a high temperature (600° C.) and pressures above atmospheric pressure, with the use of partial pressure of $O_2$ of the order of 3 bar being described.

Other studies in the scientific literature also describe the oxidation of diols, focusing essentially on the application of metallic catalysts based on gold at temperatures of the order of 70° C. to 90° C. at pressures of between 2 bar and 3 bar of pure oxygen and the addition of a base to maintain a constant pH. The yields of lactic acid are always in the range between 5% and 64% and this performance may be the reason for the comparison with systems based on platinum or palladium supported on activated charcoal [S. Demirel, P. Jern, M. Lucas, P. Claus, Catal. Today 122 (2007) 292-300; L. Prati, M. Rossi, J. Catal. 176 (1998) 552-560; C. Bianchi, F. Porta, L. Prati, M. Rossi, Top. Catal. 13 (2000) 231-236].

The document of patent CN 101225041 concerns a process which uses gold catalysts on different supports and the addition of NaOH or KOH to control the pH at 10. It is possible to obtain lactic acid, although with very low yields at the specified conditions, varying in the range between 9.7% and 32% and reaching 81% at the highest conversion of glycerine. Lactic acid is not obtained directly in free form, with subsequent stages of hydrolysis being necessary for the production of the acid, such as fermentative processes which generat solid residues to be discarded.

The document of patent EP 2 184 270 concerns a process for production of lactic acid from glyceraldehyde, using zeolite beta acid as a catalyst containing tin in the structure. The process also allows the corresponding esters to be obtained by using a suitable solvent. Thus, to obtain methyl lactate, methanol is used as a solvent. A selectivity of 16% is obtained in methyl lactate from glyceraldehyde in the presence of Sn-BETA catalyst at 100° C. over 20 hours at a pressure of argon of 20 bar and using methanol as the solvent. In these processes, no base or alkaline solution is added to control the pH, however the fact that the reaction is processed in an inert atmosphere (argon) at quite high pressures must be considered.

In a recent article [A. Tsuji, K. T. V. Rao, S, Nishimura, A. Takagaki, K. Ebitani, ChemSusChem, 4 (2011) 542-548], the use of reactions of selective oxidation of the primary hydroxyl of the glycerol or of 1,2-propanediol to glyceric acid and lactic acid is reported respectively in an aqueous medium making use of mild temperature conditions and flow of pure oxygen, without the addition of a base. To this end, Pt/hydrotalcite catalysts with different Mg/Al ratios are used but with extremely high levels of platinum, of more than 35% by weight. In the case of oxidation of the 1,2-propanediol, after 6 hours of reaction, selectivity towards lactic acid of 70% is obtained and conversion of the diol of around 65%, which gives a yield in lactic acid of 45.5%.

In most of the state of the art processes using a heterogeneous catalyst, the pH of the reaction medium has to be controlled by the continuous addition of an alkaline solution. This operation does not allow the direct production of lactic acid, but rather of its respective salt, a lactate.

This fact is an important disadvantage, as like the fermentative processes, the lactate that is produced has to be hydrolised by the addition of an inorganic acid in a subsequent operation. At this stage, large amounts of solid residue are generated, and this has to be separated and discarded, as in the biological processes. Besides the environmental impact, the need of various stages to obtain the lactic acid increases the complexity of the process, and consequently its cost.

As can be seen, on the basis of the description of this invention that follows, lactic acid is obtained in a single stage, eliminating the step of addition of alkaline solutions, with no need to control the pH, and the elimination of solid residue formation and consequently no additional separation, treatment or discarding of solid residue is necessary. These various advantages afforded entail a reduction of the costs of the process and mitigate the environmental impact, establishing an environmentally friendly process.

SUMMARY OF THE INVENTION

The invention concerns a process for the direct synthesis of lactic acid, carried out in a single stage by means of selective oxidation of 1,2-propanediol in the presence of a heterogeneous catalyst. The reaction takes place in the presence of oxygen and with a mixture of heterogeneous catalysts, specifically a first catalyst of noble metal supported in metallic oxide, and a second basic solid catalyst. The selective oxidation of the hydroxyl group of the primary carbon of the 1,2-propanediol takes place at temperatures in the range from 30° C. to 100° C., typically at atmospheric or autogenous pressure, and without the need for the addition of any base or alkaline solution. The mixture of catalysts is easily recovered by filtration at the end of the process, to be reused. The lactic acid is obtained directly, with selectivity of between 50% and 97%.

The term "direct synthesis of lactic acid" refers to a process whereby lactic acid may be obtained in a single step process, in the context of the invention this is a single step process of oxidation of 1,2-propanediol to lactic acid. The oxidation is a selective oxidation of the primary hydroxyl group. Thus, in a direct process for the synthesis of lactic acid, there is typically no requirement for a further reaction to be carried out before lactic acid is obtained. Such further reactions may include the acid hydrolysis of a lactate salt, such as is required in processes known in the art. Thus the process of the invention produces lactic acid without production of a lactate salt intermediate.

Accordingly, the invention provides a process for direct synthesis of lactic acid, which process comprises oxidation of 1,2-propanediol in the presence of oxygen and a mixture of catalysts, which mixture of catalysts comprises: a first metallic catalyst comprising a supported noble metal; and a second basic catalyst which comprises a basic oxide; and wherein the oxidation takes place at a temperature of from 30° C. to 100° C.

The invention also provides:

[1] A process for direct synthesis of lactic acid, characterised as consisting of the following stages:
Obtain a first metallic catalyst from a precursor of noble metal able to be decomposed forming the corresponding oxide in a support, then activating the first metallic catalyst by means of reduction under flow of hydrogen in a flow of 50 mL min$^{-1}$ at 350° C. for 2 hours;
Feed a reactor equipped with a reflux system and mechanical agitation, with a solution of 1,2-propanediol in different concentrations and with a physical mixture of the first metallic catalyst with a second basic catalyst, which consists of a basic oxide obtained by means of thermal decomposition;
Make the materials react by means of heating, kept within a range between 30° C. and 100° C., under agitation at a speed of between 200 rpm and 2000 rpm, with bubbling of oxygen, air or a mixture of both, with autogenous pressure between 1 bar and 5 bar;
Leave to react during approximately 6 hours and separate the products obtained, removing the mixture of heterogeneous catalysts by filtration, and separating the lactic acid directly from the aqueous phase, with selectivity between 50% and 97%, and yield of 25%.

[2] A process for direct synthesis of lactic acid, according to [1], characterised by the referred to first metallic catalyst consisting of at least one of the noble metals selected from Pt, Cu, Pd, Au, Ru, Rh, Ir, supported in a pure oxide metallic, in a mixture of metallic oxides or in aluminium silicates with zeolitic structure.

[3] A process for direct synthesis of lactic acid, according to [1] or [2], characterised by the referred to impregnation of the catalyst to be carried out from a salt precursor of platinum selected from $H_2Pt(OH)_6$, $Pt(NO_3)_4$, $Pt(NH_3)_4(NO_3)_2$, $Pt(NH_3)_4(OH)_2$, $PtCl_4$, $Pt(NH_4)_2Cl_4$, $Pt(NH_4)_2Cl_6$, $Pt(C_5H_7O_2)_2$ or a compound that decomposes forming $PtO_2$.

[4] A process for direct synthesis of lactic acid, according to [1] or [2], characterised by the level of noble metal in the catalyst varying in a range between 0.01% and 10%, preferably between 0.1% and 5% by weight.

[5] A process for direct synthesis of lactic acid, according to [1], characterised by the referred to second basic catalyst consisting of a simple basic oxide, a double basic oxide, a simple hydroxide or a double hydroxide, with a specific surface within the range 10 m$^2$g$^{-1}$ and 800 m$^2$g$^{-1}$, selected from Al, Zn, Li, Na, K, Rb, Cs, Fr, Be, Mg, Ca, Sr, Ba or a combination of these, in particular simple oxides of magnesium or calcium, mixed oxides containing Mg, Al or Zn and double hydroxide compounds of Mg, Al or Zn.

[6] A process for direct synthesis of lactic acid, according to [1], characterised by using 1,2-propanediol as a raw material in aqueous solution with concentration from 0.05 M to the pure substrate, and a flow of synthetic air (20% of $O_2$ in $N_2$ by volume) in the range between 10 mL min$^{-1}$ and 100 mL min$^{-1}$; allowing the reaction temperature to vary in the range between 30° C. and 80° C., the pressure of reaction in the interval between 1 bar and 5 bar, and mechanical agitation to be maintained at a speed between 500 rpm and 2000 rpm.

[7] A process for direct synthesis of lactic acid, according to [1], characterised by the reduction of the first metallic catalyst to be conducted in-situ in the temperature range between 30° C. and 100° C.

[8] A process for direct synthesis of lactic acid, according to [1], characterised by alternatively the reduction of the first metallic catalyst to be conducted sequentially ex-situ at a temperature between 200° C. and 500° C. and in-situ in the temperature range between 30° C. and 100° C.

[9] A process for direct synthesis of lactic acid, according to [1], characterised by the proportion between the mass of metallic catalyst and the mass of basic catalyst to be between 0.5 and 6.0, preferably between 0.6 and 4.5.

[10] A process for direct synthesis of lactic acid, according to [1], characterised by the proportion between the metallic catalyst and 1,2-propanediol to be in the range between 1:4 to 1:20 by weight.

[11] A process for direct synthesis of lactic acid, according to [1], characterised by the process to be conducted in a continuous regime, semi-continuous, in semi-batches or a combination of these, both in the gaseous phase and in the liquid phase.

DETAILED DESCRIPTION OF THE INVENTION

The process will be described in greater detail and illustrated by means of examples so that it can be well understood and evaluated. It should be pointed out, however, that such examples are merely illustrative and should not be considered as limiting the invention.

As mentioned before, the process of the invention concerns the synthesis of lactic acid by direct oxidation of 1,2-propanediol in conditions of low temperature and generally low pressure and in the presence of the physical mixture of heterogeneous catalysts, with a first catalyst typically being a noble metal supported on metallic oxide along with a second basic catalyst. Under such conditions it is possible to obtain the lactic acid directly, with selectivity of between 50% and 97%, and a yield of 25% or more, with the advantage of requiring low complexity and using less energy than is used in the known processes, enabling the use of already installed equipment normally found in industrial plants.

The process can be conducted continuously, semi-continuously, in semi-batches or a combination of these, both in the gaseous phase and in the liquid phase.

In accordance with the process of the invention for direct synthesis of lactic acid, a gaseous current selected from amongst air, pure oxygen or a mixture of both is added to a reactor equipped with a bubbling system containing an aqueous solution 0.2 M 1,2-propanediol at atmospheric pressure. This reactor also contains a mixture of solid catalysts to convert the 1,2-propanediol in the presence of oxygen, preferably into lactic acid, with a first catalyst being based on a noble metal supported on metallic oxide and a second basic catalyst.

The term "basic oxide", as used herein, refers to both metal oxides and metal hydroxides.

The process for direct synthesis of lactic acid may comprise the following stages:
  feeding a reactor, which reactor is optionally equipped with a reflux system and mechanical agitation, with 1,2-propanediol or an aqueous solution of 1,2-propanediol, and with a physical mixture of the first metallic catalyst with a second basic catalyst, which second basic catalyst comprises a basic oxide, optionally obtained by means of thermal decomposition; and
  allowing the materials to react by means of heating, kept within a range between 30° C. and 100° C., optionally under agitation at a speed of between 200 rpm and 2000 rpm, with bubbling of oxygen, air or a mixture of both, optionally with autogenous pressure between 1 bar and 5 bar.

The process for direct synthesis of lactic acid may further comprise obtaining the first metallic catalyst from a precursor of noble metal able to be decomposed by forming the corresponding oxide in a support, then activating the first metallic catalyst by means of reduction under flow of hydrogen, optionally in a hydrogen flow of 50 mL min-1 at 350° C., optionally for 2 hours.

The process for direct synthesis of lactic acid may further comprise allowing the reaction components to react for approximately 6 hours and optionally separating the products obtained by removing the mixture of heterogeneous catalysts by filtration, and separating the lactic acid directly from the aqueous phase.

The process for direct synthesis of lactic acid typically has a selectivity for lactic acid (i.e. a selectivity for oxidation of the primary hydroxyl group) of between 50% and 97%. Often the yield is greater than or equal to 25%, for instance about 25%

In accordance with the process of this invention the 1,2-propanediol is converted into lactic acid by means of an oxidation reaction of the primary carbon hydroxyl of the diol molecule, and typically comprises the following stages:
  Obtain a first metallic catalyst by impregnation or by deposition-precipitation of a precursor of the noble metal capable of decomposition to form the corresponding oxide on a support, and then activating the referred to first metallic catalyst by means of reduction, for example reduction under flow of hydrogen at a flow rate of 50 mL min$^{-1}$ at 350° C. for 2 hours;
  Feed a reactor, maintained with mechanical agitation and under reflux, with 1,2-propanediol (e.g. as pure substrate) or an aqueous solution of 1,2-propanediol at a concentration of at least 0.05 M, and with the physical mixture of the first metallic catalyst with a second catalyst of basic character, which consists of a basic metallic oxide which is typically obtained by means of thermal decomposition of a salt of the metal;
  Heat the reagents at a temperature of between 30° C. and 100° C., typically under agitation at speed, of between 200 rpm and 2000 rpm, and with passage of a flow of oxygen, air or a mixture of both in the reactional medium, typically within the range 30 mL min$^{-1}$ and 60 mL min$^{-1}$, typically with autogenous pressure of between 1 bar and 5 bar;
  Maintain the operational conditions for approximately 6 hours and separate the products obtained, typically removing the mixture of heterogeneous catalysts by filtration, and typically separating the lactic acid from the aqueous phase by distillation, obtaining, for example, selectivity of between 50% and 97%, and a yield of 25% or more.

As far as the first metallic catalyst is concerned with regard to this invention, an oxidation catalyst is used which comprises or consists of metals or a combination of metals, supported on a pure metallic oxide, a mixture of metallic oxides or on aluminium silicates with zeolitic structure. The metal is typically selected from amongst Pt, Cu, Pd, Au, Ru, Rh, Ir or a combination of these, with Pt and Pd being preferred.

In this mode the impregnation of the catalyst is carried out from a salt precursor of platinum selected from $H_2Pt(OH)_6$, $Pt(NO_3)_4$, $Pt(NH_3)_4(NO_3)_2$, $Pt(NH_3)_4(OH)_2$, $PtCl_4$, $Pt(NH_4)_2Cl_4$, $Pt(NH_4)_2Cl_6$, $Pt(C_5H_7O_2)_2$ or any other compound that decomposes forming $PtO_2$. Preferably a solution of the hexachloroplatinic acid ($H_2PtCl_6$) is used.

In another mode of the invention, a commercial platinum catalyst supported in aluminium can be used, e.g. Pt/Al$_2$O$_3$, with 5% by weight of Pt reduced previously.

The amount of noble metal in the catalyst may be in a range between 0.01% and 10%, preferably between 0.1% and 5% by weight of the first metallic catalyst.

In one mode of this invention, the second basic catalyst is used as a heterogeneous catalyst, comprising or consisting of a simple basic oxide or a double basic oxide or even a simple hydroxide or a double hydroxide, typically with a specific surface within the range of 10 m$^2$g$^{-1}$ and 800 m$^2$g$^{-1}$, which may for example contain Al, Zn, Li, Na, K, Rb, Cs, Fr, Be, Mg, Ca, Sr, Ba or a combination of these. Oxides of magnesium, calcium and barium should preferably be used.

Thus, before starting the process of direct synthesis of the lactic acid, the catalysts are prepared in accordance with techniques known by specialists in the area.

A—Preparation of the First Metallic Catalyst

The first metallic catalyst may be prepared by humid or dry impregnation or by deposition-precipitation in a support, with a solution of the precursor of the metal, followed by a stage of calcination. The precursor solution may be selected from metallic hydroxides, nitrates, chlorides, sulphates, acetates or acetyl acetonates, or another compound that decomposes forming the corresponding metallic oxide after calcination. The metal may be selected from amongst Pt, Cu, Pd, Au, Ru, Rh, Ir or a combination of these, with Pt and Pd being preferred. The level of noble metal in the catalyst may vary in a range between 0.01% and 10%, preferably between 0.1% and 5% by weight.

The support should have a high enough specific surface to guarantee good dispersion of the metal, typically varying between 50 m$^2$g$^{-1}$ and 1000 m$^2$g$^{-1}$. The support may be selected from amongst Al$_2$O$_3$, TiO$_2$, SiO$_2$ and ZrO$_2$, Nb$_2$O$_5$, CeO$_2$, MgO, ZSM-5, MCM-41 or a combination of these, preferably Al$_2$O$_3$, TiO$_2$, SiO$_2$ or ZrO$_2$.

B—Preparation of the Second Basic Catalyst

The basic catalyst may be prepared by thermal decomposition, precipitation or co-precipitation of nitrates, chlorides, sulphates, acetates or metallic acetyl acetonates, pure or in solution, depending on the method chosen, or another compound that undergoes precipitation at alkaline pH by the presence of a precipitating agent selected from hydroxides, carbonates, bicarbonates or urea. The precipitation may be carried out at constant pH or otherwise, leading to the formation of a precipitate compound by a carbonate, bicarbonate or hydro-metallic oxide, which is separated by filtration. The filtered precipitate may be calcined at a temperature of more than 300° C. to form a simple or double oxide or a mixture of oxides.

One advantage of this invention is that the reduction of the first metallic catalyst can be conducted ex-situ at temperatures between 200° C. and 500° C., or in-situ within the temperature range between 30° C. and 100° C. In this case, the catalyst is added to the solution of 1,2-propanediol kept under agitation. Alternatively the reduction may also be carried out sequentially, ex-situ and in-situ in the same ranges of temperature described.

The final catalyst used in the process consists of two parts formed by the physical mixture of the first metallic catalyst and the second basic catalyst, with a proportion by mass of the metallic catalyst and the basic catalyst varying between 0.5 and 6.0, preferably between 0.6 and 4.5.

Thus, the ratio of the mass of metallic catalyst:the mass of basic catalyst may be between 0.5:1.0 and 6.0:1.0, preferably between 0.6:1.0 and 4.5:1.0.

In one mode of this invention, the reactor is fed with the mixture of a Pt/Al$_2$O$_3$ catalyst, with 5% by weight of previously reduced Pt and simultaneously with a basic catalyst, such as MgO, in a proportion by mass of 0.625.

The synthesis of lactic acid by direct oxidation of 1,2-propanediol in a single stage may be conducted in a reactor equipped with a reflux system using as reagents pure 1,2-propanediol or an aqueous solution at different propanediol concentrations, for instance from 0.05 M, and the physical mixture of catalysts, typically in quantities to provide a relative proportion of metallic catalyst to 1,2-propanediol in the range between 1:4 by weight to 1:20 by weight, at a temperature selected in the range between 30° C. and 100° C., optionally with an autogenous pressure between 1 bar and 5 bar, and optionally under agitation in the range between 200 rpm and 2000 rpm. The oxygen is typically added to the reactor in a range of flow between 10 mL min$^{-1}$ and 100 mL min$^{-1}$ of air, of pure oxygen or of a mixture of air heated in oxygen, with this mixture being obtained via selective membranes or another suitable technology.

The lactic acid is formed in a single stage at considerable concentrations as compared with other sub-products. The selectivity of the catalyst to lactic acid varies between 50% and 97% throughout the period of reaction. Other products detected in the reaction medium are pyruvic acid and acetol.

EXAMPLES

The performance of the prepared catalysts is evaluated in experiments carried out in the laboratory in a reactor equipped with an agitator and system for bubbling, as mentioned earlier, followed by the procedure:

a) The raw material used is an aqueous solution of 1,2-propanediol at a concentration from 0.05 M, and a synthetic flow of air (20% of O$_2$ in N$_2$ by volume) in the range between 10 mL min$^{-1}$ and 100 mL min$^{-1}$.

b) The temperature of reaction allowed varies in the range between 30° C. and 80° C., and the pressure of reaction in the range between 1 bar and 5 bar, with mechanical agitation being maintained between 500 rpm and 2000 rpm.

c) The levels of the reaction solution are taken every 30 minutes and analysed by high efficiency liquid chromatography after filtration to separate the physical mixture of catalysts.

Example 1

1st Stage—Preparation of the First Metallic Catalyst

A metallic catalyst of platinum on aluminium containing 5% p/p of platinum is prepared by humid impregnation using a commercial aluminium as support and the salt precursor of the metal, hexachloro-platinic acid.

The commercial aluminium is submitted to calcination at a rate of heating of 10° C. min$^{-1}$, at a temperature that varies between room temperature and 500° C., maintaining the final temperature for 4 hours.

Later the hexachloro-platinic acid (H$_2$PtCl$_6$) is solubilised in water in a proportion suitable to obtain a level of platinum equal to 5% and adding to the already calcined support, maintaining this suspension under agitation for 1 hour at room temperature. Then the drying is done in a vacuum (0.4 mmHg) of the material at 80° C. The solid obtained stays in an oven at 100° C. for 12 hours and is then calcined at 500° C. for 4 hours, with a rate of heating of 10° C. min$^{-1}$ and synthetic flow of air with flow of 60 mL min$^{-1}$.

The metallic catalyst of platinum on aluminium containing 5% by weight of platinum is activated by heating from room temperature to 350° C., with a rate of heating of 10° C. min$^{-1}$, maintained for 2 hours at 350° C. and using a current of pure hydrogen at a flow of 50 mL·min$^{-1}$.

2nd Stage—Selection of the Second Basic Catalyst

In carrying out these experiments, simple magnesium and calcium oxides were used as the second basic catalyst.

3rd Stage—Direct Synthesis of the Lactic Acid

The oxidation reaction is conducted using an aqueous solution of 1,2-propanediol with concentration of 0.2 M. The first metallic platinum catalyst containing 5% by weight of platinum and a second basic catalyst consisting of a simple metallic oxide are used in the form of a physical mixture whose mass ratio is of 0.625. The mixture of catalysts is transferred to the reactor containing water and a flow of 50 mL min$^{-1}$ of nitrogen, admitted to the reactor to bring about its inertisation. During the inertisation, the reactor is heated to 40° C. and maintained at this temperature during the whole of the reaction.

The aqueous solution (0.2 M) of 1,2-propanediol is added to the reactor, with mechanical agitation maintained in rotation at 1000 rpm; a flow of 30 mL·min$^{-1}$ of air is bubbled, with this being considered the starting point of the reaction.

The total reaction time was of 6 hours and throughout the experiment samples were taken at regular intervals of 30 minutes. All the samples taken were analysed by high performance liquid chromatography (HPLC).

The most representative results of the conversion, selectivity and yield of lactic acid related to the simple oxides used are shown in Table 1 below:

TABLE 1

| Basic catalyst | T (° C.) | Conversion (%) | Selectivity (%) | Yield (%) |
|---|---|---|---|---|
| MgO | 40 | 67 | 65 | 44 |
| CaO | 40 | 27 | 97 | 26 |

Example 2

Similar experiments were carried out under the same conditions as the previous example and using a heterogeneous catalyst formed of the mixture of a first metallic catalyst containing 5% by weight of platinum prepared as described in Example 1, with a second basic catalyst of magnesium oxide (MgO) in order to determine the influence of the mass ratio between the catalysts on the conversion, selectivity and yield of lactic acid.

As in the previous example, samples were taken at regular intervals of 30 minutes and the total reaction time was of 6 hours. All the samples taken were analysed by high performance liquid chromatography (HPLC).

The most representative results of the conversion, selectivity and yield of lactic acid related to the simple oxides used are shown in Table 2 below.

TABLE 2

| Reaction | Mass ratio metallic/basic | T (° C.) | Conversion (%) | Selectivity (%) | Yield (%) |
|---|---|---|---|---|---|
| 1 | 0.625 | 40 | 67 | 65 | 44 |
| 2 | 1.25 | 40 | 68 | 63 | 43 |
| 3 | 2.5 | 40 | 66 | 57 | 38 |

Example 3

In this example the oxidation reaction was conducted using an aqueous solution of 1,2-propanediol with concentration of 0.2 M. Such experiments were conducted in a reactor with reflux, containing a mechanical agitator and a system for bubbling of gases. The first metallic catalyst was a catalyst containing 5% by weight of platinum, prepared as described in Example 1, and the second basic catalyst being a double lamellar hydroxide. The metallic and basic catalysts were used in the form of a physical mixture with mass ratio equal to 1. The mixture of catalysts was transferred to the reactor containing 100 mL of water and a flow of 50 mL min$^{-1}$ of nitrogen admitted to the reactor to bring about its inertisation. During the inertisation, the reactor is heated to 40° C. and maintained at this temperature during the whole of the reaction. The aqueous solution of 1,2-propanediol (0.2 M) was introduced into the reactor and a flow of 30 mL min$^{-1}$ of bubbled air was admitted to start the reaction. The mechanical agitation was maintained at the speed of 1000 rpm.

Samples were taken at regular intervals of 30 minutes throughout the experiment and the total reaction time was of 6 hours. All the samples taken were analysed by high performance liquid chromatography (HPLC), and the most representative conversion, selectivity and yield results of the double lamellar hydroxides found are shown in Table 3 below:

TABLE 3

| Reaction | Double lamellar hydroxide containing Mg and Al | T (° C.) | Conversion (%) | Selectivity of lactic acid (%) | Yield of lactic acid (%) |
|---|---|---|---|---|---|
| 1 | molar ratio $Mg^{2+}/Al^{3+}$ = 3 | 40 | 52 | 58 | 30 |
| 2 | molar ratio $Mg^{2+}/Al^{3+}$ = 5 | 40 | 61 | 60 | 37 |

Example 4

As in the previous examples, the oxidation reactions were conducted using an aqueous solution of 1,2-propanediol, 0.2 M, in a reactor provided with reflux, mechanical agitator and a system for bubbling of gases. The first metallic catalyst was a catalyst containing 5% by weight of platinum prepared as described in Example 1, and the second basic catalyst was a double lamellar hydroxide containing magnesium and aluminium with mass ratio Mg/Al equal to 3. The final catalyst was used in the form of a physical mixture. The mixture of catalysts was transferred to the reactor containing 100 mL of water and a flow of 50 mL min$^{-1}$ of nitrogen was admitted to the reactor to bring about its inertisation. During the inertisation, the reactor was heated and maintained at 40° C. temperature throughout the reaction. The aqueous solution of 1,2-propanediol (0.2 M) was then introduced to the reactor and a flow of 30 mL min$^{-1}$ of air was admitted by the bubbler, starting the reaction, with the mechanical agitation being maintained at the speed of 1000 rpm.

The total reaction time was 6 hours and throughout the experiment samples were taken at regular intervals of 30 minutes.

All the samples taken were analysed by high efficiency liquid chromatography (HPLC), the most representative conversion, selectivity and yield results of the double lamellar hydroxides found are shown in Table 4 below:

TABLE 4

| Reaction | Mass ratio metallic catalyst/ basic catalyst | T (° C.) | Conversion (%) | Selectivity of lactic acid (%) | Yield of lactic acid (%) |
|---|---|---|---|---|---|
| 1 | 1 | 40 | 52 | 58 | 30 |
| 2 | 2 | 40 | 46 | 56 | 26 |
| 3 | 4 | 40 | 43 | 55 | 24 |

The invention described here is referenced to its preferred embodiments. It should therefore be clear that the invention is not limited to these embodiments, and those with technical abilities will immediately perceive that alterations and substitutions may be adopted without deviating from the inventive concept described here.

The invention claimed is:

1. Process for direct synthesis of lactic acid, which process comprises oxidation of 1,2-propanediol in the presence of oxygen and a mixture of catalysts, which mixture of catalysts comprises: a first metallic catalyst comprising a supported noble metal; and a second basic catalyst which comprises a basic oxide
wherein: the oxidation takes place at a temperature of from 30° C. to 100° C.; and the first metallic catalyst comprises at least one of the noble metals selected from Pt, Cu, Pd, Au, Ru, Rh, Ir, supported in a pure metallic oxide, in a mixture of metallic oxides or in aluminum silicates with zeolitic structure.

2. Process for direct synthesis of lactic acid according to claim 1 which process comprises the following stages:
feeding a reactor, which reactor is optionally equipped with a reflux system and mechanical agitation, with 1,2-propanediol or an aqueous solution of 1,2-propanediol, and with a physical mixture of the first metallic catalyst with a second basic catalyst, which second basic catalyst comprises a basic oxide, optionally obtained by means of thermal decomposition; and
allowing the materials to react by means of heating, kept within a range between 30° C. and 100° C. with bubbling of oxygen, air or a mixture of both, optionally under agitation at a speed of between 200 rpm and 2000 rpm, optionally with autogenous pressure between 1 bar and 5 bar.

3. Process for direct synthesis of lactic acid according to claim 1, which process further comprises obtaining the first metallic catalyst from a precursor of noble metal capable of decomposition to form the corresponding oxide on a support, then activating the first metallic catalyst by means of reduction under flow of hydrogen, optionally in a hydrogen flow of 50 mL min-1 at 350° C., optionally for 2 hours.

4. Process for direct synthesis of lactic acid according to claim 1, which process further comprises allowing reaction for approximately 6 hours and optionally separating the products obtained by removing the mixture of heterogeneous catalysts by filtration, and separating the lactic acid directly from the aqueous phase.

5. Process for direct synthesis of lactic acid according to claim 1, which process has a selectivity between 50% and 97%, and optionally a yield of 25% or more.

6. Process for direct synthesis of lactic acid, according to claim 2, wherein the referred to precursor of a noble metal is selected from a salt precursor of platinum selected from
the group consisting of $H_2Pt(OH)_6$, $Pt(NO_3)_4$, $Pt(NH_3)_4(NO_3)_2$, $Pt(NH_3)_4(OH)_2$, $PtCl_4$, $Pt(NH_4)_2Cl_4$, $Pt(NH_4)_2Cl_6$, and $Pt(C_5H_7O_2)_2$.

7. Process for direct synthesis of lactic acid, according to claim 1, wherein the amount of noble metal in the catalyst is in a range between 0.01% and 10% by weight of the first metallic catalyst.

8. Process for direct synthesis of lactic acid, according to claim 1, wherein the referred to second basic catalyst comprises a simple basic oxide, a double basic oxide, a simple hydroxide or a double hydroxide, selected from Al, Zn, Li, Na, K, Rb, Cs, Fr, Be, Mg, Ca, Sr, Ba or a combination of these, optionally wherein the second basic catalyst has a specific surface within the range 10 $m^2g^{-1}$ and 800 $m^2g^{-1}$.

9. Process for direct synthesis of lactic acid, according to claim 1, wherein 1,2-propanediol as a raw material in aqueous solution with a concentration of greater than or equal to 0.05 M is used, and a flow of synthetic air comprising 20% of $O_2$ in $N_2$ by volume in the range between 10 mL $min^{-1}$ and 100 mL $min^{-1}$ is used; the reaction temperature is allowed to vary in the range between 30° C. and 80° C., the pressure of reaction is allowed to vary in the range between 1 bar and 5 bar, and wherein mechanical agitation is maintained at a speed between 500 rpm and 2000 rpm.

10. Process for direct synthesis of lactic acid, according to claim 2, wherein the reduction of the first metallic catalyst is conducted in-situ in the temperature range between 30° C. and 100° C.

11. Process for direct synthesis of lactic acid, according to claim 2, wherein the reduction of the first metallic catalyst is conducted sequentially ex-situ at a temperature between 200° C. and 500° C. and in-situ in the temperature range between 30° C. and 100° C.

12. Process for direct synthesis of lactic acid, according to claim 1, wherein the ratio of the mass of metallic catalyst:the mass of basic catalyst is between 0.5:1.0 and 6.0:1.0.

13. Process for direct synthesis of lactic acid, according to claim 1, wherein the ratio of the metallic catalyst:1,2-propanediol is in the range between 1:4 to 1:20 by weight.

14. Process for direct synthesis of lactic acid, according to claim 1, wherein the process is conducted in a continuous regime, semi-continuous, in semi-batches or a combination of these, both in the gaseous phase and in the liquid phase.

15. Process for direct synthesis of lactic acid, according to claim 7, wherein the amount of noble metal in the catalyst is in a range between 0.1% and 5% by weight of the first metallic catalyst.

16. Process for direct synthesis of lactic acid, according to claim 8, wherein the referred to second basic catalyst is selected from simple oxides of magnesium or calcium, mixed oxides containing Mg, Al or Zn and double hydroxide compounds of Mg, Al, or Zn.

17. Process for direct synthesis of lactic acid, according to claim 12, wherein the ratio of the mass of metallic catalyst:the mass of basic catalyst is between 0.6:1.0 and 4.5:1.0.

* * * * *

UNITED STATES PATENT AND TRADEMARK OFFICE
CERTIFICATE OF CORRECTION

PATENT NO. : 8,962,882 B2  
APPLICATION NO. : 14/087203  
DATED : February 24, 2015  
INVENTOR(S) : Fraga et al.

Page 1 of 1

It is certified that error appears in the above-identified patent and that said Letters Patent is hereby corrected as shown below:

Title page

Insert --(30)   Foreign Application Priority Data:

Oct. 25, 2012           (BR) ..........................................10 2012 207339-0--

Signed and Sealed this
Twenty-first Day of June, 2016

Michelle K. Lee
*Director of the United States Patent and Trademark Office*